United States Patent [19]

Nagai et al.

[11] Patent Number: 4,843,093

[45] Date of Patent: Jun. 27, 1989

[54] BUTYROLACTONE DERIVATIVES, PROCESS FOR PRODUCTION THEREOF AND USE THEREFOR

[75] Inventors: Yoichiro Nagai, Yamato; Taichi Nakano, Maebashi; Yutaka Oomura, Fukuoka, all of Japan

[73] Assignee: Ajinomoto Co., Inc., Tokyo, Japan

[21] Appl. No.: 55,324

[22] Filed: May 29, 1987

[30] Foreign Application Priority Data

Nov. 27, 1986 [JP] Japan .................. 61-282775

[51] Int. Cl.$^4$ .................. A61K 31/365; C07D 307/20
[52] U.S. Cl. .................. 514/473; 549/295; 549/313
[58] Field of Search .................. 549/313, 295; 514/473

[56] References Cited

PUBLICATIONS

Wermuth, "Condensation of Pyruvic, etc", CA65: 15221c (1966).

Varela et al, "β-Elimination in, etc.", CA 96: 181555k (1982).

Primary Examiner—Glennon H. Hollrah
Assistant Examiner—Patricia L. Morris
Attorney, Agent, or Firm—Oblon, Fisher, Spivak, McClelland & Maier

[57] ABSTRACT

Butyrolactone derivatives having the formula

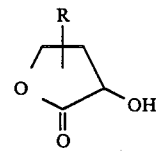

wherein R is a $C_4$–$C_{10}$ alkyl group, which have an appetite-regulating effect, a process for their production, and compositions containing them, are disclosed.

6 Claims, No Drawings

BUTYROLACTONE DERIVATIVES, PROCESS FOR PRODUCTION THEREOF AND USE THEREFOR

INDUSTRIAL FIELD

The present invention relates to novel butyrolactone derivatives which can be employed for a mediciine such as an appetite-regulating agent, a process for production of such derivatives, and a use for such derivatives as a medicine.

Prior Arts

Recently, it was made clear that β-hydroxy-γ-butyrolactone (1) and 2-butene-4-olide (2) are materials for a full stomach which regulate an appetite by working a hypothalums food-intaking center (See Yutaka Oomura, Org. Syn. Chemistry, 44, 127, 1986, Japan). However, these above compounds are low in activity, and do not show the effect unless they are administered in an amount of 1000 or more times the effective amounts in the brain.

An obese patient can suffer from myocardial infarction, diabetes mellitus, and then kidney disease.

Controlling the appetite of an obese patient is very useful in preventing above mentioned adult diseases, since such controlling is connected with lowering of high blood pressure, improvement of the system of internal secretion, and improvement of cholesterol glucose, free fatty acid, electrolytes, and the like in the blood.

On the other hand, an appetite-increasing agent to avoid a poor appetite, is useful, too. Such an agent to regulate an appetite showing a high activity therefor, is expected to be developed.

Explanation of Present Invention

A butyrolactone derivative represented by the general formula [I]

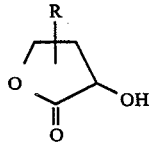

can be used as an appetite-regulating agent such as an appetite-controlling agent or an appetite-increasing agent, which can be obtained by reacting an α-halogeno-butyrolactone derivative represented by the general formula [II]

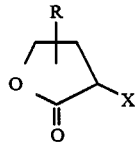

with a carbonic acid salt (a carbonate), wherein R stands for an alkyl group having 4 to 10 carbon atoms, and X stands for a halogen atom.

Examples of such alkyl groups (R) are methyl, ethyl, n-butyl, γ-isobutyl, heptyl, octyl, nonyl, etc. Particularly, α-hydroxy-Δ-alkyl-γ-butyrolactone is desirable in view of its high activity.

Examples of such halogen atoms (X) are chlorine atom, bromine atom and the like.

Examples of such carbonic acid salts (a carbonate) are potassium carbonate, sodium carbonate, etc., which can be used in the form of an aqueous solution to react with the above derivative.

Isolation and purification of the object product of the butyrolactone derivative from the reaction mixture after such reactions for production of the object compound, can be carried out easily by conventional means for isolation and purification as employed ordinarily.

The butyrolactone derivatives of the present invention are useful as appetite-regulating agents for treating, for example, obese persons and poor appetite in mammals including humans. The derivatives can be used for regulating appetite by formulating them into preparations such as tablets, capsules, and elixirs, for oral administration and into aseptic liquid preparations or aseptic suspension preparations for parenteral administration. The derivatives of the present invention can be administered to a subject need of such treatment (animals or humans) in a dosage range of 0.2 to 500 mg per subject, generally several times a day, that is, in a total daily dosage of 1 to 2000 mg. The dosage varies according to the seriousness of the disease, the body weight of the subject, and other factors known by those skilled in the art.

The foregoing typical drugs are formulated into pharmaceutical compositions stated below. About 0.2 to 500 mg of a butyrolactone derivative of the present invention, a pharmaceutically acceptable salt thereof, or a mixture of both, are blended into unit dosage forms generally acknowledged or required for pharmaceutical practice, together with pharmaceutically acceptable vehicles, carriers, excipients, binders, antiseptics, stabilizers, flavorings, and so forth. The amount of active substance in these compositions or preparations is adjusted such as to give an appropriate dosage of the prescribed range.

Specific materials which can be incorporated into tablets, capsules, and so forth, are as follows: binders such as tragacanth, gum arabic, cornstarch, and gelatin; excipients such as microcrystalline cellulose; swelling agents such as cornstarch, pregelatinized starch, and arginic acid; lubricants such as magnesium stearate; sweeteners such as sucrose, lactose, and saccharin, and flavorings such as peppermint, oil from Gaultheniaadeno thrix Maxim, and cherry. When the unit dosage form of the preparation is in the form of a capsule, a liquid carrier such as fatty oil can further be incorporated in the foregoing materials. Various other materials can be present as coating materials or a materials which vary the physical form of the unit dosage forms. For example, tablets can be coated with shellac and/or sugar. Syrups or elixirs can contain active compounds, sucrose as a sweetener, methylparaben and/or propylparaben as antiseptics, coloring matter, and a flavoring such as cherry and/or an organic flavoring agent.

Aseptic compositions for injection can be formulated according to the usual practice for preparation of pharmaceutical dosage forms, in which practice an active substance is dissolved or suspended in a vehicle such as water for injection; natural vegetable oils such as sesame oil, palm oil, peanut oil, and cotton seed oil; and synthetic fat vehicles such as ethyl oleate. A buffer, an antiseptic, and an antioxidant can further be incorporated as the occasion demands.

The invention will now be illustrated by the following examples.

EXAMPLE 1

Synthesis of α-hydroxy-γ-isobutyl-γ-butyrolactone. In a 50 ml flask with a cooling column, 1.77 g (10 mmole) of α-chloro-γ-isobutyl-γ-butyrolactone and 12 ml of 2N aqueous potassium carbonate were kept at 80 C. for 40 hours under stirring. The reaction mixture was cooled to room temperature and poured into 10 ml of 12N hydrochloric acid. The reaction product was extracted with ether and the ether extract was dried with anhydrous sodium sulfate. After removal of ether, distillation of the residue under reduced pressure gave α-hydroxy-γ-isobutyl-γ-butyrolactone. (yield 99%).

Boiling point: 119-120 C/3 mmHg Proton NMR spectrum (CCl4)

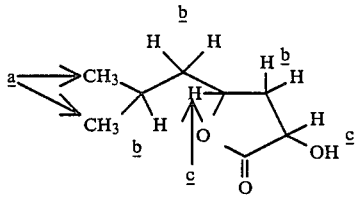

a: 0.94 ppm (d, J=6, 6H)
b: 1.25-2.85 ppm (m, 5H)
c: 4.16-4.98 ppm (m, 3H)

IR spectrum (liquid cell CCl4): (cm$^{-1}$). 3435, 2955, 2930, 2875, 1785, 1470, 1455, 1385, 1370, 1335, 1250, 1193, 1130, 955, 860, 810, 725.

Elemental Anal. C 60.03%, H 8.91%. Calcd. for $C_8H_{14}O_3$ C 60.74%, H 8.92%.

EXAMPLE 2

Synthesis of α-hydroxy-γ-butyl-γ-butyrolactone. In a 50 ml flask with a cooling column, 2.65 g (15 mmol) of α-chloro-γ-butyl-γ-butyrolactone and 17 ml of 2N aqueous potassium carbonate were kept at 80 C. for 32 hours under stirring. The reaction mixture was cooled to room temperature and poured into 10 ml of 12N hydrochloric acid. The reaction product was extracted with ether and the ether extract was dried with anhydrous sodium sulfate.

After removal of ether, distillation of the residue under reduced pressure gave α-hydroxy-γ-butyl-γ-butyrolactone (Yield, 97%).

Boiling point, 98-99 C./1.5 mmHg) Proton NMR spectrum (CCl4)

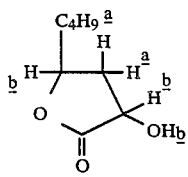

a: 0.83-3.0 ppm (m, 11H)
b: 3.9-4.67 ppm (m, 3H)

IR spectrum (KBr): (cm$^{-1}$) 3420, 2955, 2935, 2875, 1770, 1460, 1380, 1330, 1200, 1140, 1055, 960, 910.

Elemental Anal. C 61.32%, H 9.27%. Calcd. for $C_8H_{14}O_3$ C 60.74%, H 8.92%.

EXAMPLE 3

Synthesis of α-hydroxy-γ-hexyl-γ-butyrolactone In a 50 ml flask with a cooling column, 3.0 g (15 mmol) of α-chloro γ-hexyl-γ-butyrolactone and 17 ml of 2N aqueous potassium carbonate were kept at 80° C. for 40 hours under stirring. The reaction mixture was cooled to room temperature and poured into 10 ml of 12N hydrochloric acid with stirring. The reaction product was extracted with ether and the ether extract was dried over anhydrous sodium sulfate. The ether was removed and the residue was distilled under reduced pressure giving α-hydroxy-γ-hexyl-γ-butyrolactone. (Yield 91%).

Boiling point 121° C./1.5 mmHg. Proton NMR spectrum (CCl4).

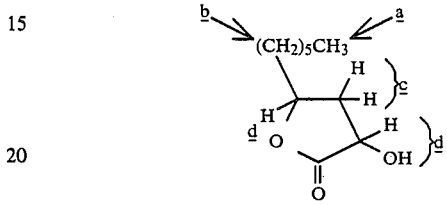

a: 0.88 ppm (t, J=5, 3H)
b: 1.1-1.77 ppm (m, 10H)
c: 1.9-3.0 ppm (m, 2H)
d: 3.87-4.83 ppm (m, 3H)

IR spectrum (KBr): (cm$^{-1}$). 3400, 2955, 2935, 2850, 1770, 1460, 1380, 1195, 1123, 995, 955, 900, 800, 725.

Elemental Anal. C 64.07%, H 9.7%. Calcd. for $C_{10}H_{18}O_3$ C 64.49%, H 9.74%.

EXAMPLE 4

Synthesis of α-hydroxy-γ-octyl-γ-butyrolactone. In a 50 ml flask with a cooling column, 3.5 g (15 mmol) of α-chloro-γ-octyl-γ-butyrolactone and 20 ml of 2N aqueous potassium carbonate were kept at 80° C. for 40 hours under stirring. The reaction mixture was cooled to room temperature and poured into 10 ml of 12N hydrochloric acid. The reaction product was extracted with ether and the ether extract was dried over anhydrous sodium carbonate. The ether was removed and the residue was distilled under reduced pressure to give α-hydroxy-γ-octyl-γ-butyrolactone (Yield 78%)

Boiling point 132°-135° C./0.5 mmHg H-NMR spectrum (CCl4)

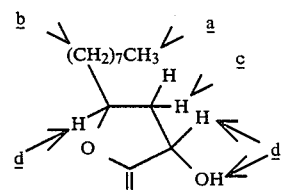

IR spectrum (KBr sandwich). 3400, 2955, 2940, 2855, 1770, 1460, 1195, 1123, 995, 955, 800, 720, cm$^{-1}$.

EXAMPLE 5

Food intake evaluation tests

Male Wistar strain rats were housed with artificial light illumination from 08:00 to 20:00 hour. The rats were deprived of food and water every day between 19:00-20:00 hour. During this period, food, water and body weight were recorded. Two hours food intake between 20:00 and 22:00 hour, night time food intake between 20:00 and 08:00 hour, and total daily food intake between 20:00 and 19:00 hour were measured. The samples were dissolved in 0.15M Nacl, adjusted to pH 7.4 with sodium bicarbonate. Injections of samples were made between 19:00 and 20:00 hour. Values are expressed as gram (mean±SD).

Results were summarized in Table 1.

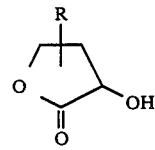

TABLE 1

| Sample | Administation | Animal | Period | Food Intake Pre-injection | Injection Day | | Post-injection |
|---|---|---|---|---|---|---|---|
| Example 3 | (100 mg/kg, ip) | (10) | 2000–2200 | 4.3 ± 1.3 | 2.1 ± 1.3 | ↓51% | 4.2 ± 1.2 |
|  |  |  | 2000–0800 | 21.6 ± 2.7 | 12.3 ± 5.8 | ↓43% | 19.2 ± 2.9 |
|  |  |  | 2000–1900 | 23.5 ± 2.2 | 15.6 ± 5.7 | ↓34% | 23.8 ± 2.5 |
| " | (75 mg/kg, ip) | (5) | 2000–2200 | 3.0 ± 0.9 | 1.5 ± 0.9 | ↓50% | 3.4 ± 0.9 |
|  |  |  | 2000–0800 | 21.3 ± 2.7 | 14.3 ± 1.8 | ↓33% | 18.3 ± 3.2 |
|  |  |  | 2000–1900 | 23.8 ± 2.6 | 17.7 ± 2.5 | ↓26% | 21.7 ± 3.3 |
| " | (50 mg/kg, ip) | (5) | 2000–2200 | 3.6 ± 1.3 | 2.2 ± 1.6 | ↓39% | 4.0 ± 0.8 |
|  |  |  | 2000–0800 | 22.0 ± 1.5 | 19.1 ± 2.0 | ↓13% | 22.5 ± 2.3 |
|  |  |  | 2000–1900 | 24.5 ± 1.5 | 22.1 ± 2.4 | ↓10% | 24.7 ± 2.4 |
| Example 2 | (100 mg/kg, ip) | (6) | 2000–2200 | 5.6 ± 2.0 | 4.2 ± 2.3 |  | 5.2 ± 3.0 |
|  |  |  | 2000–0800 | 21.2 ± 2.9 | 20.1 ± 2.5 |  | 21.2 ± 4.3 |
|  |  |  | 2000–1900 | 23.3 ± 3.1 | 23.4 ± 3.5 |  | 24.5 ± 4.1 |
| Example 1 | (100 mg/kg, ip) | (10) | 2000–2200 | 4.1 ± 1.3 | 4.6 ± 1.3 |  |  |
|  |  |  | 2000–0800 | 23.1 ± 2.2 | 22.6 ± 2.3 |  |  |
|  |  |  | 2000–1900 | 25.3 ± 1.5 | 25.1 ± 2.2 |  |  |
| Example 4 | 100 mg/kg | (3) | 2000–0800 | 22.6 ± 1.5 | 9.7 ± 9.2 | ↓57% |  |
| " | 75 mg/kg | (3) |  | 23.2 ± 4.7 | 16.5 ± 2.6 | ↓29% |  |
| " | 50 mg/kg | (3) |  | 24.0 ± 3.1 | 18.5 ± 2.3 | ↓22% |  |
| " | 25 mg/kg | (3) |  | 23.1 ± 2.3 | 23.7 ± 1.2 | — |  |

We claim:

1. A butyrolactone compound of the formula:

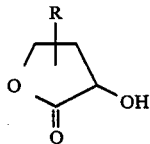

wherein R is an alkyl group of 6 to 10 carbon atoms.

2. The butyrolactone compound of claim 1, wherein group R is hexyl or octyl.

3. An appetite-regulating composition, comprising: a therapeutically effective amount of a butyrolactone compound of the formula:

wherein R is an alkyl group of 6 to 10 carbon atoms, in combination with a pharmaceutically acceptable excipient.

4. The composition of claim 3, wherein said composition provides a dosage of the therapeutically active compound ranging from 1 to 2000 mg per subject per day.

5. The composition of claim 3, wherein group R is a hexyl or octyl radical.

6. The composition of claim 3, wherein the dosage range of administered active compound is 0.2 to 500 mg of a single dose per subject.

* * * * *